(12) United States Patent
Hwang et al.

(10) Patent No.: US 7,846,461 B2
(45) Date of Patent: Dec. 7, 2010

(54) CLIMAPROOF COSMETIC COMPLEX

(75) Inventors: Donna Hui-Ing Hwang, Leonia, NJ (US); Domnica Cernasov, Ringwood, NJ (US); Ralph Macchio, Sparta, NJ (US)

(73) Assignee: Coty B.V., Haarlem (NL)

( * ) Notice: Subject to any disclaimer, the term of this patent is extended or adjusted under 35 U.S.C. 154(b) by 631 days.

(21) Appl. No.: 10/576,804

(22) PCT Filed: Oct. 21, 2004

(86) PCT No.: PCT/EP2004/012089

§ 371 (c)(1), (2), (4) Date: Apr. 21, 2006

(87) PCT Pub. No.: WO2005/039512

PCT Pub. Date: May 6, 2005

(65) Prior Publication Data

US 2007/0135535 A1   Jun. 14, 2007

(30) Foreign Application Priority Data

Oct. 23, 2003  (DE) .............................. 103 50 322

(51) Int. Cl.
*A61K 8/02* (2006.01)
*C08L 31/00* (2006.01)
*C08F 2/38* (2006.01)

(52) U.S. Cl. ........................ 424/401; 525/94; 526/72

(58) Field of Classification Search .................. 424/401
See application file for complete search history.

(56) References Cited

U.S. PATENT DOCUMENTS

| 5,219,560 | A | * | 6/1993 | Suzuki et al. ................. 424/63 |
| 6,019,962 | A | * | 2/2000 | Rabe et al. .................... 424/64 |
| 6,103,245 | A |   | 8/2000 | Clark et al. |
| 6,264,933 | B1 |  | 7/2001 | Bodelin et al. |
| 6,324,703 | B1 | * | 12/2001 | Chen .............................. 2/458 |
| 6,391,290 | B1 | * | 5/2002 | Fowler ........................ 424/59 |
| 6,524,565 | B1 |  | 2/2003 | Loginova et al. |
| 2003/0165451 | A1 | | 9/2003 | Lennon et al. |
| 2004/0005283 | A1 | | 1/2004 | Cersanov et al. |

FOREIGN PATENT DOCUMENTS

| EP | 1013256 |   | 6/2000 |
| GB | 2086893 A |  | 5/1982 |
| KR | 2002069596 A | * | 9/2002 |
| WO | WO 0217875 |  | 3/2002 |
| WO | WO 03009821 |  | 2/2003 |
| WO | WO 2004066918 |  | 8/2004 |

* cited by examiner

*Primary Examiner*—Sreeni Padmanabhan
*Assistant Examiner*—Layla Soroush
(74) *Attorney, Agent, or Firm*—Millen, White, Zelano & Branigan, P.C.

(57) ABSTRACT

The present invention refers to a climaproof cosmetic complex having a long-time moisture-retaining effect and water resistance. The complex comprises (in % by weight) 0.1-90% of a gelled oil composition consisting of an oil component and a polymer component; 0.1-80% of a topic water-repellent substance; 0.01-20% of a water-absorbing powder having a particle size of 1 to 100 μm; 0.01-20% of a thickening agent; and 0.1-50% of organic solvents, carrier substances, or mixtures thereof.

20 Claims, 1 Drawing Sheet

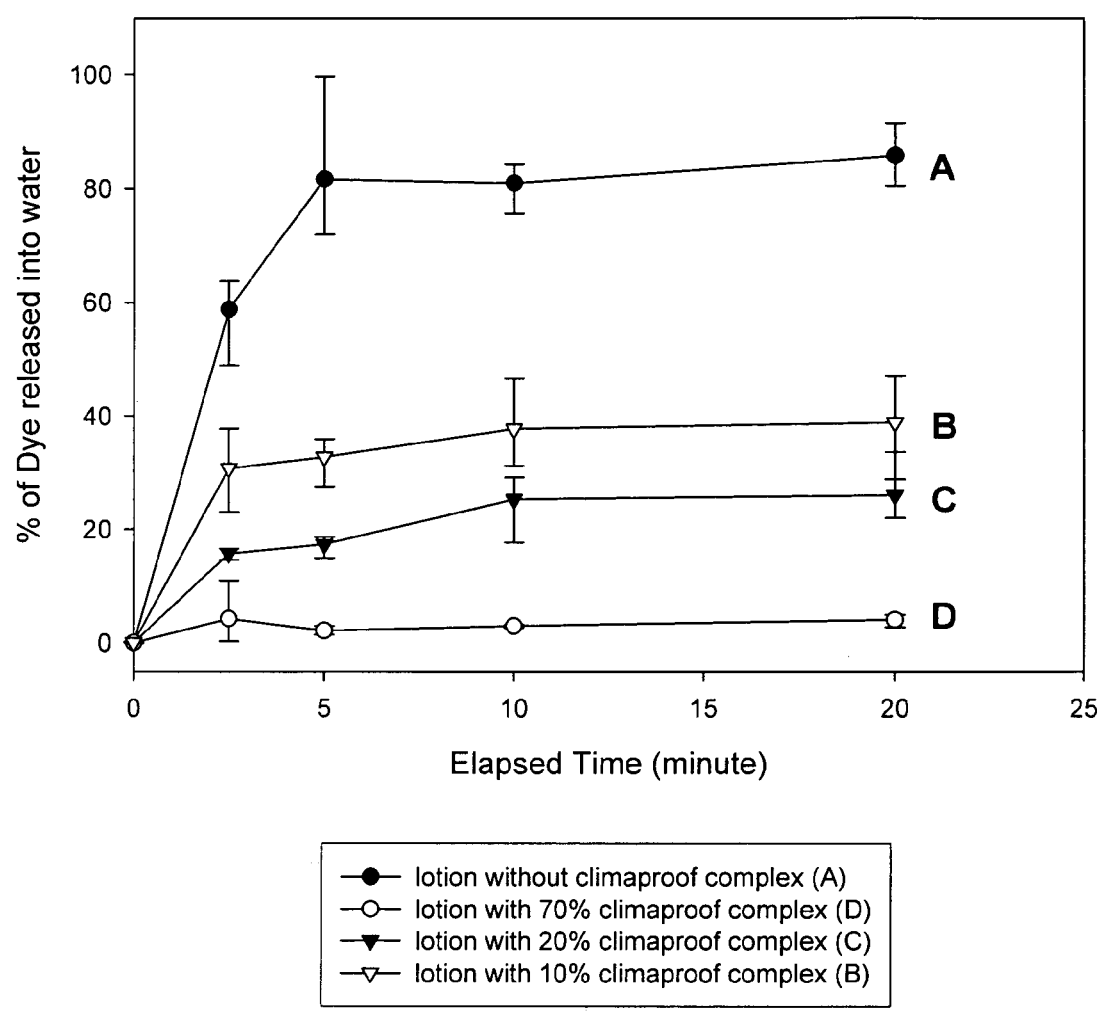

CLIMAPROOF COSMETIC COMPLEX

The present invention refers to a climaproof cosmetic complex having a long-time moisture-retaining effect and water resistance.

From the state of the art, water-resistant products are known which are used in the field of decorative cosmetics. EP 1013256 B1 describes a mascara in which an aqueous phase is dispersed in a liquid fat phase wherein said aqueous phase also contains a film-forming polymer system formed as solid particles as well as lamellar filling substances. EP 925778 B1 describes an aqueous emulsion of solid silicone compounds in combination with film-forming polymers representing a water-resistant care product for the skin and lips. EP 1064930 B1 describes i.a. a make-up consisting of an aqueous phase with fibres dispersed therein and a cross-linked, solid, elastomeric polyorganosiloxane.

It is an object of the present invention to provide a climaproof cosmetic complex having a long-time moisture-retaining effect and at the same time excellent water resistance and transfer resistibility.

According to the present invention, said climaproof cosmetic complex comprises:

0.1-90% by weight of a gelled oil composition consisting of an oil component and a polymer component, which polymer component is selected from the group consisting of tri-block copolymers, star polymers, radial polymers, multi-block polymers of polystyrene, polyethylene, polyvinyl chloride, polyisoprene, polybutadiene, ethylene/butadiene copolymers, ethylene/propylene copolymers, ethylene/butylene copolymers, ethylene-propylene/diene copolymers, styrene-ethylene/propylene copolymers, styrene-ethylene/butadiene copolymers, styrene-isoprene copolymers, styrene-butadiene copolymers, styrene-ethylene/propylene-styrene copolymers, styrene-ethylene/butadiene-styrene copolymers, styrene-isoprene-styrene copolymers, styrene-butadiene-styrene copolymers, and mixtures thereof;

0.1-80% by weight of a topic water-repellent cross-linked polyester consisting of polyvalent alcohols and mono-or dicarbon acids;

0.01-20% by weight of a water-absorbing powder having a particle size of 1 to 100 μm, which powder is selected from the group consisting of natural plant powders rich in cellulose, maltodextrine, starch, starch/polyacrylates copolymers, silicon dioxide, silicates, synthetic polymers made from acrylic monomers and mixtures thereof;

0.01-20% by weight of a thickening agent; and 0.1-50% by weight of organic solvents, carrier substances, or mixtures thereof, each related to the total weight of the complex.

Climaproof complex is a skin protection complex against weather-related enviromental damage. The complex forms an adhesive waterresistant film on skin and prevents the penetration of the foreign compounds such as dusts and pollution accomplished by rain or snow into skin. The complex has a sustained water retaining capability that prevents skin dehydration by wind or sun.

A preferred range for the gelled oil composition in the climaproof complex is 20 to 70% by weight.

Advantageously, the polymer share in the oil composition is in the range of 1:5 to 1:50 polymer component:oil component.

The oil component is e.g. selected among hydrocarbons, fatty alcohols, natural and synthetic oils, esters, ethers, and mixtures thereof.

The polymer component is, as mentioned above, selected from tri-block copolymers, star polymers, radial polymers, multi-block polymers, and combinations thereof. These synthetic polymers or copolymers are e.g. polystyrene, polyethylene, polyvinyl chloride, polyisoprene, polybutadiene, ethylene/butadiene copolymers, ethylene/propylene copolymers, ethylene/butylene copolymers, ethylene-propylene/diene copolymers, styrene-ethylene/propylene copolymers, styrene-ethylene/butadiene copolymers, styrene-isoprene copolymers, styrene-butadiene copolymers, styrene-ethylene/propylene-styrene copolymers, styrene-ethylene/butadiene-styrene copolymers, styrene-isoprene-styrene copolymers, styrene-butadiene-styrene copolymers, and mixtures thereof. Special preferred are one or more di-block-copolymers, one or more tri-block copolymers and mixtures thereof.

Particularly preferred for the polymer component are 20-70% by weight.

A prerequisite for the topic water-repellent substance is to have a skin affinity, to be insoluble in water and to have a long endurance in water. Furthermore, it is capable of retaining powder-like substances and thus to protect the upper layers of the epidermis.

The topic water-repellent substance has a molecular weight ranging from 600 to 8,000 and is a cross-linked polyester consisting of polyvalent alcohols and mono- or dicarbon acids. Polyvalent alcohols include, for example, trimethylpentane diol, glycerine or diethylene glycol.

The acids include, for example, adipic acid and fatty acids. A preferred water-repellent substance is e.g. Trimethylpentanediol/Adipic acid/Glycerine Copolymer.

The gelled oil composition and the topic water-repellent substance are complementary in their properties in such a manner that the strong skin affinity, transfer resistibility and stickiness of the topic water-repellent substance and the water-resistant and film-forming properties of the gelled oil composition result in an extremely transfer-resistant and thus climate-resistant (climaproof) film the overall effect of which exceeds the individual effect thus providing a synergistic effectiveness.

Preferably, the water-absorbing powder is based on natural plant origins that are rich in cellulose and/or silica, e.g. bamboo powder, cotton powder, wood powder, guar gum, xanthan gum etc. or on other substances such as maltodextrine, starch, starch derivatives and polyacrylates including such ones like a starch/acrylamide/sodium acrylate copolymer. Silicon dioxide (silica) and its derivatives such as aluminum magnesium silicate and calcium silicate as well as synthetic polymers made from acrylic monomers may also be used for this purpose.

Particularly preferred for the water absorbing powder are 2-8% by weight.

An oil-based complex such as 12-hydroxy stearic acid, high-molecular hydrocarbons, polyethylene, natural and synthetic waxes, acids and esters having melting points between 60 and 100° C. may preferably be used as thickening agent.

Suitable solvents or carrier substances include polar and non-polar oils, hydrocarbons, ether, esters as well as alcohols such as alkoxylated alcohols, polyvalent alcohols and polyols. Examples include ethyl alcohol, isopropanol, propylene glycol, dipropylene glycol, ethylene glycol, glycerine, diacetine, triacetine, isopropyl palmitate, isododecane, isohexadecane, triglycerides and mineral oil.

In addition, the complex may contain 0.01 to 50% by weight cross-linked silicone polymers bringing about a better hydrophobic wash-off resistibility. Examples include silicones forming a polymer network; cross-linked dimethylpolysiloxane elastomers, and mixtures thereof in volatile silicone oil; dimethyl/vinyl dimeticone cross-polymer;

dimeticone/phenyl vinyl dimeticone cross-polymer; cross-linked silicone polyether copolymers with cyclopentasiloxane; dimeticone cross-polymer.

The complex according to the present invention can be integrated as an essential component into decorative cosmetic products such as foundations, lotions, lipsticks, eye shadow, lip glosses, make-up's, rouges and also creams, cleanser, body shampoos, sunscreens, after-shaves and deodorant preparations, and the complex provides such products with the desired climaproofness, an improved transfer behaviour, endurance on the skin, and water-repellent behaviour.

These decorative cosmetic products may contain further active agents and auxiliary substances. For instance, agents for improving skin penetration may be included which allow a better deposition of active agents. Such intensifiers include ethoxydiglycol, panthenol, and phytanetriol.

The percentage of the climaproof cosmetic complex in a decorative cosmetic product may range from 0.1 to 99.9% by weight. Its use in a range from 5 to 40% by weight is preferred, special preferred are 5-20%.

In addition to the complex according to the present invention, the decorative cosmetic products may contain further auxiliary substances and active agents such as e.g. pigments, colourants, antioxidants, preservatives, other moisture-retaining agents, softeners, fragrances, stabilisers, adstringents, cell turn-over promoters, cell proliferation stimulators, anti-inflammatory agents, anti-microbial agents, hormone regulators, enzyme inhibitors, UV adsorbers, sunscreens etc.

The invention further concerns the use of a cosmetic complex in cosmetic products, which complex comprises 0.1-90% by weight of a gelled oil composition consisting of an oil component and a polymer component;

0.1-80% by weight of a topic water-repellent substance;

0.01-20% by weight of a water-absorbing powder having a particle size of 1 to 100 μm;

0.01-20% by weight of a thickening agent; and 0.1-50% by weight of organic solvents, carrier substances, or mixtures thereof, for skin protection against weather-related environmental damage.

The share of the complex in a cosmetic product is in the range of 5 to 80% by weight, preferred 5-40% by weight, related to the total weight of the cosmetic composition.

The present invention will hereinafter be further explained by means of examples. All percentages are to mean % by weight unless specified otherwise.

In the attached drawing

FIG. 1: shows a diagram with % of dye released into water through an area (film) protected by the inventive complex.

EXAMPLE 1

Climaproof Complex I

| | (viscosity = 8,000–10,000 Pa · s (cps)) | |
|---|---|---|
| Phase | Ingredients | % (wt./wt.) |
| A | Isododecane, ethylene/propylene/styrene copolymer, and butylenes/ethylene/styrene copolymer | 40–50 |
| | Isododecane | 20–30 |
| B | Trimethylpentanediol/adipic acid/glycerin Copolymer | 5–15 |
| | Methylheptyl isostearate | 5–15 |
| C | Di-C12–15 alkyl fumarate | 0.5–1.5 |
| | Behenoyl stearic acid | 0.5–1.5 |
| | Cyclomethicoan and dimethicone copolymer | 5–15 |

| | -continued | |
|---|---|---|
| | (viscosity = 8,000–10,000 Pa · s (cps)) | |
| Phase | Ingredients | % (wt./wt.) |
| D | Bamboo powder | 1–5 |
| E | Preservatives | 0.3–1.0 |
| | Fragrance | 0.3–1.2 |
| | Total | 100.0 |

The procedure for formulating the complex is the following:

The ingredients of Phase A are added into a clean, dry, stainless steel kettle equipped with a mixer. With slow mixing, the mixture is heated to 80° C. and the temperature maintained until the batch is uniform with no undissolved raw materials present.

In a separate stainless steel vessel, the ingredients of Phase B are premixed until uniform. Phase B is added to Phase A with moderate mixing speed and maintained at 75° C. until the batch is uniform. During continuous mixing the ingredients of Phase C are added to Phase A+B and the batch temperature maintained at 75° C. until uniform. The heating is discontinued and cooling the batch to 50° C. started. When batch temperature reaches 50° C., phase D is added to the main batch kettle. Mixing well until batch is uniform and homogeneous followed.

Phase E is added to the main batch and is mixed well until the batch is uniform and homogeneous.

EXAMPLE 2

Climaproof Complex II

| | viscosity = 12,000–15,000 Pa · s (cps) | |
|---|---|---|
| Phase | Ingredients | % (wt./wt.) |
| A | Hydrogenated isobutene, hydrogenate styrene/isoprene copolymer, and hydrogenate styrene/butadiene copolymer | 55–65 |
| | Isododecane | 10–20 |
| B | Trimethylpentanediol/adipic acid/glycerin copolymer | 10–20 |
| | Hydrogenated polydecene | 5–15 |
| C | Polyethylene | 0.5–1.5 |
| D | Modified starch | 1–5 |
| E | Preservatives | 0.3–1.0 |
| | Fragrance | 0.3–1.2 |
| | Total | 100.0 |

The procedure for formulation is according to example 1.

EXAMPLE 3

Climaproof Complex III

| | viscosity = 22,000–30,000 Pa · s (cps) | |
|---|---|---|
| Phase | Ingredients | % (wt./wt.) |
| A | Isononyl isononanoate, ethylene/propylene/styrene copolymer, and butylenes/ethylene/styrene copolymer | 20–30 |
| | Isopropyl palmitate | 20–30 |

-continued

| | viscosity = 22,000–30,000 Pa · s (cps) | |
|---|---|---|
| Phase | Ingredients | % (wt./wt.) |
| B | Adipic acid/diethylene glycol/glycerin copolymer | 15–25 |
| | Hydrogenated polydecene | 15–25 |
| C | Synthetic wax | 2.5–10 |
| D | Bamboo powder | 1–5 |
| E | Preservatives | 0.3–1.0 |
| | Fragrance | 0.3–1.2 |
| | Total | 100.0 |

The procedure for formulation is according to example 1.

EXAMPLE 4

Comparative Test 1

There was prepared a basic lotion. To the basic lotion different parts of the climaproof complex I was added.

| | Formula of basic lotion | |
|---|---|---|
| Phase A | water | 75–85 |
| | glycerine USP | 1–5 |
| | Acrylates/C10–30 Alkyl Acrylate Crosspolymer | 0.1–0.5 |
| | Polysorbate 60 | 0.2–0.7 |
| Phase B | mineral oil | 3–8 |
| | stearyl alcohol | 0.5–4 |
| | cetyl alcohol | 1–5 |
| | glyceril monostearate | 1–5 |
| | octyl palmitate | 1–5 |
| Phase C | water | 1–5 |
| | triethanolamine 99% | 0.1–0.5 |
| Phase D | phenonip | 0.8–1.2 |
| | Total | 100.0 |

The procedure for formulating the basic lotion is the following: The ingredients of Phase A are added into a clean, dry, stainless steel kettle equipped with a mixer. With slow mixing, one begins to heat the batch to 75° C. and maintains the temperature until the batch is uniform with no undissolved raw materials present. In a separate stainless steel vessel, the ingredients of Phase B are premixed and the batch is heated to 75° C. until uniform. Phase B is added to Phase A with moderate to high mixing speed. The batch temperature is maintained at 75° C. and the batch is mixed for 20 minutes or longer until uniform. After continued mixing the ingredients of Phase C are added to Phase A+B and the batch temperature maintained at 75° C. until uniform. The heating is discontinued and one began to cool the batch to 50° C. When batch temperature reaches 50° C., phase D is added to the main batch kettle. Mixing well until batch is uniform and homogeneous followed.

With the basic lotion the test lotions A, B, C and D are prepared; 0, 10, 20 and 70% by weight of the climaproof complex were included, respectively.

0.1 gram of each sample was evenly spread on a glass slide that contains 20 mg of 0.2% blue #1. The whole slide was dried at 50° C. for 20 minutes and then cooled to room temperature.

Testing: Each prepared slide was immersed into twenty-five grams of water for a desired time period. After removing the slide, the remained water solution was analyzed by the UV-VIS spectrophotometer to measure the color intensity.

Test Results:

TABLE 1

Climaproof Film Protection:
Prevention dye (%) released into water

| Min | no complex (A) | 70% complex (D) | 20% complex (C) | 10% complex (B) |
|---|---|---|---|---|
| 0 | 0.06 ± 0.13 | 0.0001 ± 0.03 | 0.03 ± 0.15 | 0.03 ± 0.15 |
| 2.5 | 58.78 ± 8.55 | 4.23 ± 5.84 | 15.69 ± 1.01 | 30.78 ± 7.38 |
| 5 | 81.70 ± 15.55 | 2.19 ± 0.77 | 17.34 ± 2.09 | 32.78 ± 4.54 |
| 10 | 81.01 ± 4.70 | 2.99 ± 0.32 | 25.31 ± 6.56 | 37.73 ± 7.97 |
| 20 | 85.77 ± 5.52 | 4.07 ± 1.17 | 26.04 ± 6.60 | 38.84 ± 9.21 |

The results are shown in FIG. 1. The significant decreasing of % of dye released in water by a lotion with 10% climaproof complex by nearly 50% demonstrates the excellent water-resistibility and clima-protecting characteristics of the complex according to the present invention.

EXAMPLE 5

Comparative Test 2

There was prepared a basic lotion according to example 4. To the basic lotion, 10% of climaproof complex I, II and III was included, respectively.

0.1 gram of sample was evenly spread on a glass slide that contains 20 mg of 0.2% blue #1. The whole slide was dried at 50° C. for 20 minutes and then cooled to room temperature.

The test procedure is according to example 4. The percentages of dye retained in the film were calculated as following: % Dye retained in the film=100%−(color intensity in the remained water solution/color intensity of 20 mg of 0.2% blue #1 in 25 g of water)

Test Results:

TABLE 2

Climaproof Film Protection:
retained dye (%) in protective film

| 10% complex I A | 10% complex II B | 10% complex III C | No complex D |
|---|---|---|---|
| 74.0 ± 6.6 | 39.2 ± 9.5 | 38.9 ± 4.2 | 14.2 ± 5.5 |

The results show that with 10% complex, about 2.5 to 5 times of protection was received in comparing to the basis lotion without complex.

EXAMPLE 6

Climaproof Complex IV

| | Viscosity = 85,000–150,000 Pa · s (cps) | |
|---|---|---|
| Phase | Ingredients | % (wt./wt) |
| A | Hydrogened isobutene, hydrogenated styrene/isoprene copolymer and hydrogenate styrene/butadiene copolymer | 60–70 (65) |
| | Isododecane | 3–12 (4) |
| | Hydrogenated polydecene | 5–10 (7.5) |
| B | Trimethylpentanediol/adipic acid/glycerin copolymer | 15–25 (20) |
| C | Polyethylene | 0.5–1.5 (0.5) |
| D | Maltrin | 1–5 (2) |
| E | Preservatives | 0.5–1 (0.8) |
| | Fragrance | 0.5–1 (0.8) |
| | Total | 100.0 |

The procedure for formulating Complex IV is according to example 4. The figures in brackets are a specific formula, also in the following examples.

EXAMPLE 7

Skin Protection Creme

There was prepared a basic skin protective cream with the following formula:

| Phase | Ingredients | % (wt./wt.) |
|---|---|---|
| A | Water | 75–85 |
| | Propylene glycol | 2–8 |
| | Glycereth-7 triacetate | 1–5 |
| | PEG/PPG-4/12 dimethicone | 0.3–1 |
| B | Polyacrylamide | 0.3–1.5 |
| | C13–14 isoparaffin | 0.1–1 |
| | Laureth-7 | 0.1–0.5 |
| | Dimethicone | 5–10 |
| | Isohexadecane | 1–5 |
| C | Water | 1–5 |
| | Triethanolamine 99% | 0.1–0.5 |
| D | Preservatives | 0.3–1 |
| | Fragrance | 0.3–1 |
| | UV absorber | 3–8 |
| | Total | 100.0 |

The procedure for formulating the basic cream is the following:

The ingredients of Phase A are added into a clean, dry, stain-less steel kettle equipped with a mixer. With slow mixing, one begins to heat the batch to 75° C. and maintains temperature until batch is uniform. In a separate stainless steel vessel, the ingredients of Phase B are premixed and the batch is heated to 75° C. until uniform. Phase B is added to Phase A with moderate to high mixing speed. While maintain batch temperature at 75° C., mixing is continued for 20 minutes or longer until the batch is uniform. The heating is discontinued and one began to cool the batch to 50° C. When batch temperature reaches 50° C., phase C is added to the main batch kettle. Mixing well until batch is uniform and homogeneous followed. The ingredients of Phase D are added to the main batch kettle until uniform and homogeneous.

With the basic cream ingredients, 30% of the climaproof complex IV was added. After that a test according to comparative test 2 followed.

Test Results:

TABLE 3

| Climaproof Film Protection: retained dye (%) in protective film | |
|---|---|
| 30% complex IV A | No complex B |
| 57.6 ± 7.3 | 0.3 ± 2.2 |

The results show that with complex, about 5 times of protection was received in comparing to the one without complex.

EXAMPLE 8

Climaproof Complex V

| | Viscosity = 400,000–800,000 Pa · s (cps) | |
|---|---|---|
| Phase | Ingredients | % (wt./wt.) |
| A | Isononyl isononanoate and ethylene/propylene/styrene copolymer, and butylenes/ethylene/styrene copolymer | 35–50 (40) |
| | Hydrogenated polydecene | 20–35 (28) |
| B | Adipic acid/diethylene glycol/glycerin copolymer | 15–25 (20) |
| | Isopropyl palmitate | 2–8 (5) |
| C | Synthetic wax | 1–5 (3) |
| D | Xantham gum and guar gum | 1–5 (3) |
| E | Preservatives | 0.5–1 (0.8) |
| | Fragrance | 0.5–1 (0.2) |
| | Total | 100.0 |

The procedure for formulating the complex is according to example 6.

EXAMPLE 9

Sensual Body Wash

There was prepared a basic sensual body wash. Formula of basic body wash is following:

| Phase | Ingredients | % (wt./wt.) |
|---|---|---|
| A | Water | 65–80 |
| | Glycerine | 1–5 |
| | Propylene glycol | 0.5–3 |
| | Sodium laureth sulfate | 10–20 |
| | Sodium lauryl sulfate | 1–3 |
| | Coco-betaine | 1–5 |
| | PPG-1-PEG-9 lauryl glycol ether | 0.5–5 |
| | PEG-7 glyceryl cocoate | 0.5–5 |
| | PEG-55 propylene glycol oleate | 0.5–5 |

-continued

| Phase | Ingredients | % (wt./wt.) |
|---|---|---|
| B | Sodium chloride | 0.5–5 |
|   | Citric acid (adjusted pH to 5.5–6.0) | q.s. |
| C | Preservatives | 0.3–1 |
|   | Fragrance | 0.3–1 |
|   | UV absorber | 4–12 |
|   | Total | 100.0 |

The ingredients of Phase A are added into a clean, dry, stain-less steel kettle equipped with a mixer. With slow mixing one begins to heat the batch to 65-70° C. and maintains the temperature until the batch is uniform. Phase B is added to Phase A with slow to moderate mixing speed and the batch is mixed for 20 minutes or longer until uniform. The heating is discontinued and one begins to cool the batch to 50° C. When batch temperature reaches 50° C., phase C is added to the main batch kettle. Mixing well until batch is uniform and homogeneous followed.

With the basic body wash ingredients, 30% of the climaproof complex V was added. After that a test according to comparative test 2 followed.

Test Results:

TABLE 4

Climaproof Film Protection:
retained dye (%) in protective film

| 30% complex V<br>A | No complex<br>B |
|---|---|
| 33.6 ± 12.7 | 8.1 ± 2.7 |

With complex, about 4 times of protection was received in comparing to the one without complex.

EXAMPLE 10

Complex VI

Viscosity = 50,000–90,000 Pa·s (cps)

| Phase | Ingredients | % (wt./wt.) |
|---|---|---|
| A | Isopropyl palmitate, ethylene/propylene/styrene copolymer, and butylenes/ethylene/styrene copolymer | 40–50 (45) |
|   | Isododecane | 25–35 (30) |
| B | Trimethylpentanediol/adipic acid/glycerine copolymer | 15–25 (20) |
| C | Synthetic wax | 2.5–8 (2) |
| D | Nature cotton powder | 1–5 (2) |
| E | Preservatives | 0.3–1 (0.8) |
|   | Fragrance | 0.3–1 (0.2) |
|   | Total | 100.0 |

The Procedure for formulating Complex is according to example 6.

EXAMPLE 11

Sunscreen with SPF20

| Phase | Ingredients | %(wt./wt.) |
|---|---|---|
| A | Water | 55–65 |
|   | Propylene glycol | 2–8 |
|   | Sodium polyacrylate | 1–5 |
|   | Tween 60 | 1–5 |
| B | Ethylhexyl methoxy cinnamate | 6–7.5 |
|   | Benzophenone-3 | 3.5–4.5 |
|   | Ethylhexyl salicylate | 4.5–5.5 |
|   | Octocrylene | 6–7.5 |
|   | PPG-15 stearyl ether | 1–5 |
|   | Alkyl siloxane wax | 1–5 |
|   | Hexyl laurate | 0.5–3 |
|   | Polyglyceryl-4 isostearate | 0.5–3 |
|   | Cetyl PEG/PPG-70/1 dimethicone | 0.5–3 |
|   | Trilaureth-4 phosphate | 1–5 |
|   | Dimethicone | 1–10 |
| C | Preservatives | 0.3–1 |
|   | Fragrance | 0.3–1 |
|   | UV absorber | q.s. |
|   | Total | 100.0 |

The procedure for formulating the basic sunscreen ingredients is the following:

The ingredients of Phase A are added into a clean, dry, stain-less steel kettle equipped with a mixer. With slow mixing, one begins to heat batch to 65-70° C. and maintains temperature until batch is uniform. In a separate stainless steel vessel, the ingredients of Phase B are premixed and the batch is heated to 65° C. until uniform. Phase B is added to Phase A with moderate to high mixing speed. While maintain batch temperature at 65° C., one continues to mix for 20 minutes or longer until the batch is uniform. The heating is discontinued and one begins to cool the batch to 50° C. When batch temperature reaches 50° C., phase C is added to the main batch kettle. Mixing well until batch is uniform and homogeneous followed.

With the basic cream ingredients, 30% of the climaproof complex VI was added. After that a test according to comparative test 2 followed.

Test Results:

TABLE 5

Climaproof Film Protection:
retained dye (%) in protective film

| 30% complex VI<br>A | No complex<br>B |
|---|---|
| 49.3 ± 13.5 | 19.4 ± 11.3 |

With complex, about 2.5 times of protection was received in comparing to the one without complex.

Preferred viscosities for the climaproof complex of the invention are in the range of 50,000 und 500,000 Pa·s, measured according to the Brookfield method with spindles TC/TD/TE at 25° C. and in the range of 50-75% of the spindle speeds.

The invention claimed is:

1. A climaproof cosmetic complex, which comprises
   (i) 0.1 to 90% by weight of a gelled oil composition consisting of an oil component and a polymer component, which is a tri-block copolymer, a star polymer, a radial polymer, a multi-block polymer of polystyrene, polyethylene, polyvinyl chloride, polyisoprene, polybutadiene, an ethylene/butadiene copolymer, an ethylene/propylene copolymer, an ethylene/butylene copolymer, an ethylene-propylene/diene copolymer, a styrene-ethylene/propylene copolymer, a styrene-ethylene/butadiene copolymer, a styrene-isoprene copolymer, a styrene-butadiene copolymer, a styrene-ethylene/propylene-styrene copolymer, a styrene-ethylene/butadiene-styrene copolymer, a styrene-isoprene-styrene copolymer, a styrene-butadiene-styrene copolymer, or a mixture thereof;
   (ii) 0.1 to 80% by weight of a water-repellent cross-linked polyester having a molecular weight of 600 to 8000 and consisting of polyvalent alcohol and dicarbonic acid monomers;
   (iii) 0.01 to 20% by weight of a water-absorbing powder having a particle size of 1 to 100 μm, which powder is a natural plant powder rich in cellulose, maltodextrine, starch, a starch/polyacrylate copolymer, a synthetic polymer made from an acrylic monomer or mixtures thereof;
   (iv) 0.01 to 20% by weight of a thickening agent; and
   (v) 0.1 to 50% by weight of an organic solvent, a carrier substance, or a mixture thereof,
   wherein said cosmetic complex is water resistant and contains essentially no emulsifier.

2. A climaproof complex according to claim 1, wherein the amount of gelled oil composition is 20 to 70% by weight.

3. A climaproof complex according to claim 1, wherein the polymer share in the oil composition is in the range of 1:5 to 1:50 polymer component:oil component.

4. A climaproof complex according to claim 1, wherein the oil component is a hydrocarbon, a fatty alcohol, a natural or synthetic oil, an ester, an ether, or a mixture thereof.

5. A climaproof complex according to claim 1, wherein the polymer is a di-block copolymer, a tri-block copolymer or a mixture thereof.

6. A climaproof complex according to claim 1, wherein the range for the water-repellent substance is 5 to 30% by weight.

7. A climaproof complex according to claim 1, wherein the complex contains 0.01 to 50% by weight of cross-linked silicone polymer.

8. A cosmetic composition comprising 5 to 80% by weight, related to the total weight of the cosmetic composition, of a climaproof complex according to claim 1; and the remaining to 100% by weight further cosmetically acceptable substances.

9. A cosmetic composition according to claim 8 comprising 10 to 40% by weight of the climaproof complex.

10. A cosmetic composition according to claim 8 which is a composition for skin protection against weather-related environmental damage.

11. A cosmetic composition according to claim 8 which is a composition of a decorative cosmetic foundation, lotion, lipstick, eye shadow, lip gloss, make-up or rouge.

12. A climaproof complex composition according to claims 1 which contains no emulsifying agent.

13. A climaproof complex according to claim 1, wherein the amount of polymer component is 20 to 70% by weight.

14. A climaproof complex according to claim 1, wherein said polyvalent alcohol is trimethylpentane diol, glycerine or diethylene glycol.

15. A climaproof complex according to claim 1, wherein the amount of said water-absorbing powder is 2-8% by weight.

16. A climaproof complex according to claim 1, wherein said water absorbing powder is bamboo powder, cotton powder, wood powder, guar gum, xanthan gum, maltodextrine, starch, a starch/acrylamide/sodium acrylate copolymer, silicon dioxide (silica), aluminum magnesium silicate, or a synthetic polymer made from an acrylic monomer.

17. A climaproof complex according to claim 1, wherein said water repellent substance is a trimethylpentanediol/adipic acid or a glycerine copolymer.

18. A climaproof cosmetic complex, which comprises
   (i) 0.1 to 90% by weight of a gelled oil composition consisting of an oil component and a polymer component, which is a tri-block copolymer, a star polymer, a radial polymer, a multi-block polymer of polystyrene, polyethylene, polyvinyl chloride, polyisoprene, polybutadiene, an ethylene/butadiene copolymer, an ethylene/propylene copolymer, an ethylene/butylene copolymer, an ethylene-propylene/diene copolymer, a styrene-ethylene/propylene copolymer, a styrene-ethylene/butadiene copolymer, a styrene-isoprene copolymer, a styrene-butadiene copolymer, a styrene-ethylene/propylene-styrene copolymer, a styrene-ethylene/butadiene-styrene copolymer, a styrene-isoprene-styrene copolymer, a styrene-butadiene-styrene copolymer, or a mixture thereof;
   (ii) 0.1 to 80% by weight of water repellent crosslinked trimethylpentanediol/adipic acid/glycerin copolymer having a molecular weight of 600 to 8000;
   (iii) 0.01 to 20% by weight of a water-absorbing powder having a particle size of 1 to 100 μm, which powder is a natural plant powder rich in cellulose, maltodextrine, starch, a starch/polyacrylate copolymer, a synthetic polymer made from an acrylic monomer or mixtures thereof;
   (iv) 0.01 to 20% by weight of a thickening agent; and
   (v) 0.1 to 50% by weight of an organic solvent, a carrier substance, or a mixture thereof,
   wherein said cosmetic complex is water resistant and contains essentially no emulsifier.

19. A climaproof complex according to claim 18, wherein the amount of gelled oil composition is 20 to 70% by weight.

20. A climaproof complex according to claim 18, wherein the polymer share in the oil composition is in the range of 1:5 to 1:50 polymer component:oil component.

* * * * *